United States Patent [19]

Takekoshi et al.

[11] Patent Number: 5,386,037

[45] Date of Patent: Jan. 31, 1995

[54] TRISSTANNOXANES USEFUL FOR POLYMERIZING MACROCYCLIC POLY(ALKYLENE DICARBOXYLATE) OLIGOMERS

[75] Inventors: Tohru Takekoshi, Scotia; Eric J. Pearce, Ballston Lake, both of N.Y.

[73] Assignee: General Electric Company, Schenectady, N.Y.

[21] Appl. No.: 262,793

[22] Filed: Jun. 20, 1994

[51] Int. Cl.$^6$ .............................................. C07F 7/22
[52] U.S. Cl. .................................. 549/206; 549/210; 549/212
[58] Field of Search ..................... 549/206, 210, 212

[56] References Cited

U.S. PATENT DOCUMENTS

| | | | |
|---|---|---|---|
| 3,969,319 | 7/1976 | Hutton et al. | 524/178 |
| 5,039,783 | 8/1991 | Brunelle et al. | 528/272 |
| 5,214,158 | 5/1993 | Brunelle et al. | 549/267 |
| 5,231,161 | 7/1993 | Brunelle et al. | 528/272 |
| 5,321,117 | 6/1994 | Brunelle et al. | 528/272 |

OTHER PUBLICATIONS

Liu et al., Polymer Preprints, Am. Chem. Soc., 33(1), 1111–1112 (1993).

*Primary Examiner*—Samuel A. Acquah
*Attorney, Agent, or Firm*—William H. Pittman

[57] ABSTRACT

Novel trisstannoxanes are prepared by the reaction of a dialkyltin oxide with a trihydroxy compound such as 1,1,1-tris(hydroxymethyl)propane. They may be employed as catalysts for the preparation of branched polyesters from macrocyclic polyester oligomers. They are less susceptible than previously known catalysts to the presence of acidic impurities in the oligomer compositions.

5 Claims, No Drawings

TRISSTANNOXANES USEFUL FOR POLYMERIZING MACROCYCLIC POLY(ALKYLENE DICARBOXYLATE) OLIGOMERS

BACKGROUND OF THE INVENTION

This invention relates to the polymerization of macrocyclic polyester oligomer compositions. More particularly, it relates to an improved genus of catalysts for such polymerization which is capable of producing novel branched polyesters.

The preparation of macrocyclic poly(alkylene dicarboxylate) oligomers and their polymerization to linear polyesters is described in U.S. Pat. Nos. 5,039,783, 5,214,158 and 5,231,161 and in copending, commonly owned applications Ser. Nos. 07/702,577 and 07/978,583. The catalysts employed for such polymerization include various organotin compounds and titanate esters.

Polymerization using these catalysts is quite successful and affords polyesters having excellent properties and a wide variety of potential applications. However, the catalysts are somewhat sensitive to impurities present in the macrocyclic polyesters, particularly acidic impurities which can include water, hydroxy compounds and carboxylic acids and their anhydrides.

In the presence of such impurities, the catalyst may be partially deactivated and polymerization may be incomplete or may yield polymers with low weight average molecular weights. Attempts to increase polymer yield by increasing the proportion of catalyst in the polymerization mixture cause significant further reductions in the molecular weight of the linear polymer, since the catalyst becomes part of the polymer end group and increased amounts of catalyst compete for the same proportions of structural units in the macrocyclic oligomers.

Another problem sometimes encountered with linear polyesters prepared from macrocyclic oligomers, particularly when employed in fiber-reinforced composites, is a tendency to flow or "creep" under high load. This property is detrimental to the use of such polyesters under high load conditions, such as for the fabrication of automobile frames which must carry large weights and be extremely rigid and dimensionally stable.

It would be desirable, therefore, to develop improved catalysts with high activity for the polymerization of macrocyclic oligomers containing increased proportions of impurities, especially acidic impurities. It would be further desirable to convert macrocyclic oligomer compositions to branched polyesters having improved dimensional stability, for use as load-bearing members in automobiles and the like.

SUMMARY OF INVENTION

The present invention provides a novel genus of organotin compounds which, when used as catalysts, produces polyesters of high molecular weight and high dimensional stability from macrocyclic oligomers. Said oligomers and polyesters may be employed in the fabrication of fiber-reinforced composites and the like. The polyester products include a novel class of branched polyesters, whose proportion in the product may be easily varied and which contribute to dimensional stability.

The invention includes trisstannoxanes having the formula

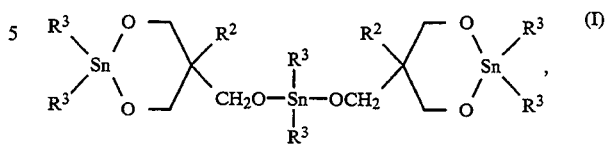

wherein $R^2$ is a $C_{1-4}$ primary alkyl radical and $R^3$ is a $C_{1-10}$ alkyl radical.

DETAILED DESCRIPTION PREFERRED EMBODIMENTS

In the trisstannoxanes of formula I, each $R^3$ is a $C_{1-10}$ alkyl radical, preferably a primary alkyl radical such as methyl, ethyl, n-butyl, n-hexyl, n-octyl, 2-ethylhexyl or n-decyl. The $C_{3-10}$ radicals are preferred. The $R^2$ radicals may be methyl, ethyl, n-propyl or n-butyl and are preferably methyl or ethyl.

The trisstannoxanes of this invention may be prepared by the reaction of a dialkyltin oxide of the formula $(R^3)_2SnO$ with a triol of the formula $R^2(CH_2OH)_3$, such as 1,1,1-tris(hydroxymethyl)ethane or 1,1,1-tris(hydroxymethyl)propane, in a molar ratio of at least about 1.2:1 and preferably about 1.25–1.75:1. The reaction is preferably conducted in solution in a substantially non-polar solvent such as toluene and at a temperature in the range of about 100°–150° C. An inert atmosphere such as nitrogen is usually employed and water is removed as it is formed, preferably as an azeotropic mixture with the solvent employed.

The preparation of the trisstannoxanes of the invention is illustrated by the following example.

EXAMPLE 1

A mixture of 2.68 grams (20 mmol.) of 1,1,1-tris(hydroxymethyl)propane, 10.83 grams (30 mmol.) of dioctyltin(IV) oxide and 25 ml. of toluene was heated under reflux in a nitrogen atmosphere in a 3-necked flask equipped with a Dean-Stark trap, with removal of water as an azeotropic mixture with toluene. After refluxing for 1 hour, the trap was replaced with another trap filled with 3A molecular sieves and refluxing was continued for 4 hours. The resulting solution was filtered under nitrogen while hot and the solvent was removed by distillation. The residue was dried under vacuum at 100° C. Upon cooling, the desired bis[(5-ethyl-2,2-dioctyl-2-stanna-1,3-dioxacyclohexane)-5-methyleneoxy]dioctyltin in impure form solidified to a waxy solid having a melting point of 78°–83° C. The crude yield was 12.5 grams (96.3% of theoretical). A portion of the product, upon recrystallization from hexane, melted at 91°–93° C.

The trisstannoxanes of this invention are useful as macrocyclic polyester oligomer polymerization catalysts. The oligomers which are polymerized thereby comprise structural units of the formula

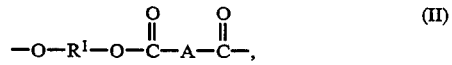

wherein $R^1$ is an alkylene or mono- or polyoxyalkylene radical containing a straight chain of about 2–8 atoms and A is a m- or p-linked monocyclic aromatic or alicyclic radical.

Said macrocyclic polyester oligomers may be prepared by contacting at least one diol of the formula HO—R¹—OH and at least one diacid chloride of the formula

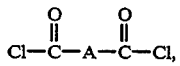

under substantially anhydrous conditions and in the presence of a substantially water-immiscible organic solvent, with at least one unhindered tertiary amine; said contact being conducted at a temperature from about −25° to about +25° C. This procedure is described in detail in the aforementioned patents and applications, and it is therefore deemed unnecessary to provide a detailed explanation herein. In most instances, the products are mixtures of macrocyclic oligomers having differing degrees of polymerization.

The macrocyclic polyester oligomers are converted to high molecular weight polyesters by contact with the polystannoxanes of this invention at a temperature in the range of about 160°–300° C., preferably 160°–250° C., with the macrocyclic polyester oligomer polymerization catalyst. The latter is typically employed in the amount of about 0.01–2.0 and preferably about 0.05–1.0 mole percent based on structural units in the oligomers. This method of producing polyesters is disclosed and claimed in copending, commonly owned application Ser. No. 08/262,795.

The polyesters thus produced have a number of advantageous properties. First, they have high molecular weights even when prepared from oligomer mixtures with a relatively high proportion of acidic impurities.

Second, the polymers are highly branched by reason of the mechanism of their preparation. Catalysts of formula II initiate polymerization by incorporating ester units between the oxygen and carbon atoms in their molecular structure. Since there are multiple oxygen atoms, each associated with a tin atom, and since the tin atoms become incorporated in the polymer molecule, the result is a highly branched structure which may be represented schematically by the formula

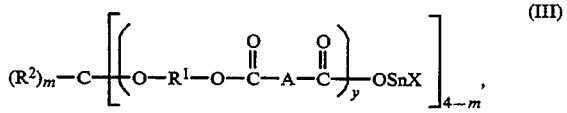

wherein $R^1$, $R^2$ and A are as previously defined, X is a linear or branched organic end group, y has an average value of at least about 10 and m is 0 or 1. Branched polyesters of this formula are disclosed and claimed in copending, commonly owned application Ser. No. 08/262,799.

The previously disclosed catalysts, including those described in the aforementioned patent and application, produce linear polyesters. It is contemplated to employ a mixture of such a catalyst with a trisstannoxane of formula I to produce a mixture of branched and linear polyesters. The proportions of the two types of catalysts may be varied to afford the desired degree of branching.

The preparation of polyesters from macrocyclic oligomers using the trisstannoxanes of this invention is illustrated by the following examples.

EXAMPLES 2–4

The macrocyclic oligomers employed were prepared by the reaction of 5 millimoles of ethylene glycol and 95 millimoles of 1,4-butanediol with 100 millimoles of terephthaloyl chloride, substantially as described in the aforementioned patents and applications. Solutions in methylene chloride of the macrocyclic oligomers were divided into two samples; Sample A was washed first with aqueous acid, then with aqueous base and finally with deionized water, and Sample B with aqueous acid and water only. The methylene chloride was then removed by vacuum stripping and the products were pre-dried for 15 minutes at 100° C. under vacuum and then heated to 190° C. for 15 minutes with magnetic stirring, to form melts.

The molten oligomer melts were returned to atmospheric pressure by addition of nitrogen, polymerization catalysts in the desired proportion were added by injection and the mixtures were maintained at 190° C. for 20 or 30 minutes. During polymerization the products crystallized. The yields and molecular weights of the polyesters obtained were determined by gel permeation chromatography relative to standard polystyrene. The results are given in the following table, in comparison with controls employing two catalysts not part of the invention. The catalysts are identified in Table VII as follows:

| Example | Catalyst Identity | Mole % | Time, min. | % yield | Mw | Mw/Mn |
|---|---|---|---|---|---|---|
| 2A | II | 0.5 | 30 | 98 | 517,600 | 6.76 |
| 2B | II | 0.5 | 20 | 96 | 162,600 | 2.90 |
| 3A | III | 0.25 | 30 | 100 | 227,000 | 2.93 |
| 3B | III | 0.25 | 30 | 71 | 99,600 | 2.10 |
| 4A | III | 0.5 | 30 | 100 | 384,000 | 6.84 |
| 4B | III | 0.5 | 30 | 98 | 117,600 | 3.04 |
| Control 1A | IV | 0.5 | 30 | 100 | 115,300 | 2.07 |
| Control 1B | IV | 0.5 | 30 | 100 | 76,600 | 1.93 |
| Control 2A | V | 0.25 | 30 | 100 | 97,100 | 1.87 |
| Control 2B | V | 0.25 | 30 | 58 | 49,200 | 1.94 |
| Control 3A | V | 0.5 | 30 | 100 | 62,700 | 2.54 |
| Control 3B | V | 0.5 | 30 | 86 | 45,800 | 2.20 |

I: Formula II, $R^3$ = octyl, Z = C.
II: Formula II, $R^2$ = ethyl, $R^3$ = octyl, Z has formula III.
III: Formula II, $R^2$ = ethyl, $R^3$ = n-butyl, Z has formula III.
IV: Dioctyltin bis(2-ethylhexoxide).
V: Tetra-2-ethylhexyl titanate.

The results in the table show that the trisstannoxanes of this invention afford polymers with uniformly high weight average molecular weights, even when the relatively impure B oligomer samples were employed. By contrast, the controls when employed with B samples afforded polymers of relatively low molecular weight. The higher molecular weight dispersities (Mw/Mn) of the polymers formed by the trisstannoxanes of this invention are believed to be the result of their highly branched structures.

What is claimed is:

1. A trisstannoxane having the formula wherein $R^2$ is a $C_{1-4}$ primary alkyl radical and $R^3$ is a $C_{1-10}$ alkyl radical.

2. A trisstannoxane according to claim 1 wherein each $R^3$ is a $C_{3-10}$ n-alkyl radical.

3. A trisstannoxane according to claim 2 wherein each $R^3$ is n-butyl.

4. A trisstannoxane according to claim 2 wherein each $R^3$ is octyl.

5. A trisstannoxane according to claim 1 wherein $R^2$ is methyl or ethyl.

* * * * *

UNITED STATES PATENT AND TRADEMARK OFFICE
CERTIFICATE OF CORRECTION

PATENT NO. : 5,386,037

DATED : January 31, 1995

INVENTOR(S) : Tohru Takekoshi and Eric J. Pearce

It is certified that error appears in the above-indentified patent and that said Letters Patent is hereby corrected as shown below:

Column 4, line 26 "in Table VII" should be deleted; in line 42, "I. Formula II, $R^3$ = octyl, Z=C" should be deleted; line 43 should read as follows:

II: Formula I, $R^2$ = ethyl, $R^3$ = octyl.

III: Formula I, $R^2$ = ethyl, $R^3$ = n-butyl.

Signed and Sealed this

Twenty-seventh Day of June, 1995

Attest:

BRUCE LEHMAN

*Attesting Officer*      *Commissioner of Patents and Trademarks*